(12) United States Patent
Gondaliya et al.

(10) Patent No.: US 10,583,101 B2
(45) Date of Patent: Mar. 10, 2020

(54) LIPID FORMULATIONS OF CARMUSTINE

(71) Applicant: EMCURE PHARMACEUTICALS LIMITED, Bhosari, Pune (IN)

(72) Inventors: Deepak Pragjibhai Gondaliya, Pune (IN); Hiren Pravinbhai Patel, Pune (IN); Arpan Suresh Chudasama, Pune (IN); Neha Manubhai Patel, Pune (IN); Mukund Keshav Gurjar, Pune (IN)

(73) Assignee: EMCURE PHARMACEUTICALS LIMITED, Bhosari, Pune (IN)

( * ) Notice: Subject to any disclaimer, the term of this patent is extended or adjusted under 35 U.S.C. 154(b) by 0 days.

(21) Appl. No.: 16/462,622

(22) PCT Filed: Nov. 22, 2017

(86) PCT No.: PCT/IB2017/057328
§ 371 (c)(1),
(2) Date: May 21, 2019

(87) PCT Pub. No.: WO2018/096466
PCT Pub. Date: May 31, 2018

(65) Prior Publication Data
US 2019/0298671 A1    Oct. 3, 2019

(30) Foreign Application Priority Data

Nov. 25, 2016  (IN) .............. 201621040316

(51) Int. Cl.
*A61K 31/175*   (2006.01)
*A61K 9/127*    (2006.01)
*A61K 9/19*     (2006.01)
*A61K 9/51*     (2006.01)

(52) U.S. Cl.
CPC ............ *A61K 31/175* (2013.01); *A61K 9/127* (2013.01); *A61K 9/1277* (2013.01); *A61K 9/19* (2013.01); *A61K 9/5123* (2013.01)

(58) Field of Classification Search
None
See application file for complete search history.

(56) References Cited

U.S. PATENT DOCUMENTS

2010/0068251 A1 * 3/2010 Ali .................. A61K 9/127
                                                    424/450

FOREIGN PATENT DOCUMENTS

| CN | 1110134   |   | 10/1995 |
|----|-----------|---|---------|
| CN | 1683016   |   | 10/2005 |
| CN | 101143130 |   | 3/2008  |
| CN | 101444482 |   | 6/2009  |
| CN | 102198100 | * | 9/2011  |
| CN | 102198100 A | * | 9/2011  |
| JP | 05221852  |   | 8/1993  |

OTHER PUBLICATIONS

Takenaga, Mitsuko, "Application of Lipid Microspheres for the Treatment of Cancer" Advanced Drug Delivery Reviews, vol. 20, No. 2-3 Jul. 1996, pp. 209-219 (abstract only).
PCT International Search Report for PCT/162017/057328, dated Feb. 6, 2018.
PCT Search Strategy for PCT/IB2017/057328, dated Feb. 6, 2018.
PCT Written Opinion of the International Searching Authority for PCT/IB2017/057328, dated Feb 6. 2018.

* cited by examiner

*Primary Examiner* — Nannette Holloman
(74) *Attorney, Agent, or Firm* — Florek & Endres PLLC

(57) ABSTRACT

The present invention relates to a pharmaceutical lipid composition comprising nitrosoureas and process for its preparation. In particular, the compositions of present invention are useful in the treatment of brain cancers having improved physicochemical and pharmacokinetic characteristics.

18 Claims, No Drawings

LIPID FORMULATIONS OF CARMUSTINE

This application is the U.S. National Stage filing of International Patent Application Number PCT/IB2017/057328, filed on Nov. 22, 2017, which claims the benefit of Indian Provisional Applications No. 201621040316 filed on 25 Nov. 2016, which is hereby incorporated by reference in its entirety.

FIELD OF THE INVENTION

The present invention relates to a pharmaceutical lipid suspension composition comprising nitrosourea and its use for the treatment of cancer. In particular, the invention relates to a stable lipid suspension composition comprising carmustine for injection and its use for the treatment of cancer. The present invention also relates to a method for preparation of such pharmaceutical compositions.

BACKGROUND OF THE INVENTION

Brain tumor is a mass of unnecessary cells growing in the brain or central spine canal. There are two basic kinds of brain tumors—primary brain tumors and metastatic brain tumors. Primary brain tumors start and tend to stay, in the brain. Metastatic brain tumors begin as cancer elsewhere in the body and spread to the brain. Brain tumors are also classified as "benign" or "malignant" based on degree of malignancy or aggressiveness of a brain tumor. Depending on the degree of malignancy, tumors are classified into Grade I, Grade II, Grade III and Grade IV.

According to published reports, nearly 70,000 new cases of primary brain tumors are diagnosed each year and around 10% of these are children between the ages of 0-19. It is reported that brain and central nervous system tumors are the most common cancers among children ages 0-19. There are nearly 700,000 people in the United States living with a brain tumor. There are more than 120 types of brain tumors identified till date.

The main treatments for brain or spinal cord tumors are surgery, radiotherapy and chemotherapy. These treatments may be used alone or in combination. Chemotherapy uses anti-cancer drugs (cytotoxic agents) to destroy cancer cells. They work by disrupting the growth of cancer cells. Chemotherapy drugs can be delivered orally (by mouth as a pill or liquid), intravenously (by infusion into a vein), topically (as a cream on the skin), or through Injection or direct placement (via a lumbar puncture or device placed under the scalp).

Nitrosureas have been generally utilized as single agent treatment chemotherapy or in established combination therapy with other approved chemotherapeutic agents for many years against primary brain tumors. Nitrosourea includes chemotherapeutic agents such as Chlorozotocin (DCNU), Carmustine (BCNU), Lomustine (CCNU), Nimustine and Ranimustine. Amongst them, Carmustine (bischloroethyl nitrosurea, BCNU or BiCNU) is a one of the leading nitrosurea drug for treatment of brain cancers owing to its ability to cross blood-brain barrier and excellent activity against brain tumors.

Carmustine alkylates DNA and RNA, interfering with their synthesis and functions. It also binds and modifies (carbamoylates) glutathione reductase, which consequently leads to cell death. Chemically, it is 1,3-bis (2-chloroethyl)-1-nitrosourea and has the following structural formula:

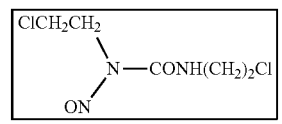

Carmustine is highly soluble in alcohol and lipids but poorly soluble in water wherein it readily gets hydrolyzed in water at pH >6. Carmustine is commercially available as a sterile lyophilized powder for injection under the tradename BiCNU® and in single dose vials containing 100 mg of lyophilized powders of carmustine. Dehydrated alcohol is co-packaged with the active drug product as a sterile diluent for constitution. The lyophilized carmustine appears as a pale yellow dry flake or a dry congealed mass. Prior to injection, the lyophilized carmustine is reconstituted with a co-packed sterile diluent and the solution is then further diluted with water. The reconstitution results in a clear, colorless to yellowish solution which may be further diluted with 5% Dextrose Injection, USP. However, the infusion of ethanol in BiCNU® formulation causes infusion toxicity and hypersensitivity reactions in patients.

Further, the conventional lyophilized formulation of carmustine is associated with frequent and serious toxicity in the form of delayed myelosuppression, Further, following IV infusion, it is rapidly taken up by the tissues but has shown to be rapidly degraded, with no intact drug detectable after 15 minutes. Therefore, the drug is associated with high toxicity and low selectivity, which in turn reduces the application of this drug for treatment of cancer.

To overcome and/or to reduce such side effects, it is the need of the hour to device a more efficient drug delivery system which can increase pharmaceutical efficacy accompanied by the concomitant decrease of side effects.

Lipoidal drug delivery system is one of such promising tool to tackle the problems in prior use, as stated above and many researchers have tried to develop a lipoidal formulation of carmustine. Few of the published formulations are as follows:

CN101143130 relates to a parenteral formulation of carmustine in the form of a stable oil-in-water emulsion. The composition comprises of pharmaceutically effective amount of carmustine, oil, a surfactant and water for injection. The invention also discloses the method of preparation of the said oil-in-water emulsion.

CN1110134 relates to an injectable, liposomal formulation and the process for its preparation. In the disclosed process, the fat-soluble pharmaceutically active ingredient and the liposome matrix are dissolved in an organic solvent to obtain lipid-soluble liquor; or alternatively, only the liposome matrix is dissolved in the organic solvent, and then a water-soluble liquid pharmaceutically active ingredient is added to the lipid-soluble liquor. The organic solvent is then removed from the liquor by using vacuum drying method and then nitrogen gas is charged into it.

Further, CN101444482, provide sustained-release injectable formulations containing a nitrosourea drug, which comprises of sustained-release microspheres and solvents. The sustained-release microspheres each comprise an anti-cancer-active component selected from nitrosourea drugs (such as nimustine and carmustine) and/or topoisomerase inhibitors, and a sustained-release agent. The solvents are common solvents or special solvents containing suspending agent. However, such processes are complex and expensive.

CN 1683016 discloses a process for preparation carrier particles containing surface transferrin for glioma-targetedchemotherapy. Biodegradable polymers like polylactic acid, polyglycolic acid, polycaprolactone or copolymer of lactic acid and glycolic acid and chemotherapeutic drugs such as carmustine, adriamycin or taxols are dissolved in acetone, acetonitrile or dimethyl sulfoxide; and the solution is emulsified in a solution of transferrin or combined with transferrin chemically after co-dialysis with cholesterol modified glucosan dialdehyde to prepare the drug-carrying polymer particle containing surface transferrin. Such particles may be injected into tumor cavity for targeted release of the drug.

Thus, there is a need for an improved, robust carmustine formulating process.

OBJECTS OF THE INVENTION

An object of the present invention is to provide a stable lipid suspension formulation of Carmustine.

Another object of the present invention is to provide a process for preparation of stable lipid suspension formulation of Carmustine.

Further object of the present invention is to provide a process for preparation of a stable lipid suspension formulation of Carmustine, wherein said process is simple, cost-effective and commercially viable.

SUMMARY OF THE INVENTION

The present invention is directed to a stable pharmaceutical composition of carmustine. Typically, the present invention provides a lipid suspension composition of carmustine, which is useful in the treatment of various neoplastic diseases.

In one aspect, the present invention provides a novel pharmaceutical composition comprising carmustine and lipids. In some embodiments of the pharmaceutical composition, the ratio of the carmustine to lipid is from 1.0:1.0 to 1.0:25. Typically, the pharmaceutical compositions of the present invention are provided as lyophilized powder suitable for dilution and may contain carmustine up to 50% by weight of the composition, preferably about 25% by weight of the composition and more preferably from 0.1 to 10% by weight of the composition.

In another aspect, the pharmaceutical composition may further comprise one or more other suitable excipients, which include but are not limited to buffers, isotonic agents, pH adjusters, antioxidants, reducing agents, antimicrobial preservatives, freeze-dried excipients, stabilizers.

In still another aspect, the present invention provides a novel pharmaceutical composition comprising carmustine, lipids antioxidant, isotonic agents and buffers.

In further embodiment, the pharmaceutical composition may comprise one or more pharmaceutically acceptable vehicle carriers therein. Such carriers may be selected from saline, sterile water, Ringer's solution, buffered saline, dextrose solution, maltodextrin solution, glycerol, ethanol and a combination thereof and are provided as lipid suspension formulation, which are ready to administer.

According to some embodiments, the carmustine composition contains not more than about 0.3%, more preferably not more than about 0.2%, even more preferably not more than about 0.1% of known degradation product of carmustine, at time zero after preparation. The know impurities of carmustine are 1,3-bis(2-chloroethyl)urea, which is referred as carmustine impurity A. The total known and unknown impurities in the present composition are less than about 1.0%.

In a further aspect, the present invention provides a method for preparing a pharmaceutical composition of carmustine. Typically, the process comprises the steps of dissolving lipid and other excipients in a buffered solution, followed by addition of carmustine, homogenizing the solution and lyophilizing the same.

In yet another aspect, the present invention provides a method of treating a patient in need, which comprises the steps of reconstituting the lyophilized carmustine lipid suspension composition into an aqueous solution, optionally followed by diluting the resulting solution, and administering an effective amount of the aqueous carmustine solution to a mammal in need thereof. The patient in need may suffer from brain tumors, multiple myeloma, Hodgkin's disease, and non-Hodgkin lymphoma.

DETAILED DESCRIPTION OF THE INVENTION

The present invention, in the preferred embodiment is directed to a Lipid Suspension formulation of carmustine. The term "lipid suspension" as used herein refers generically to a dispersion of complexes formed from a suitable lipid and carmustine in a liquid medium. The term "lipid suspension" is also used to indicate the complexes formed from a suitable lipid and carmustine, which is capable of being dispersed in a liquid medium to form suspension. Therefore, the lipid suspension, can also be used to refer the lyophilized powder of complexes formed from a suitable lipid and carmustine. Typically, according to present invention, carmustine is present in the encapsulated form and and/or in complexed form with the lipid. The carmustine lipid complex refers to particles of undefined structure which consist of a suitable lipid and an encapsulated or complexed carmustine.

The term "suitable lipid" as used herein refers to a compound which is capable of forming complexes with carmustine, and is substantially non-toxic when administered at the necessary concentrations. Suitable lipids generally have a polar or hydrophilic end, and a non-polar or hydrophobic end. Suitable lipids include without limitation lecithin, Sphingosylphosphorylcholine, soybean phosphatidylcholine, dipalmitate phosphatidylcholine, hydrogenated soy lecithin, phosphatidic acid or phosphatidylserine ethanolamine, egg phosphatidylcholine, egg phosphatidyl-glycerol, dimyristoyl-phosphatidyl-glycerol, dimyristoyl-phosphatidylcholine, hydrogenated soy phosphatidylcholine and other hydroxycholesterol or aminocholesterol derivatives. The preferred lipid is soya phosphatidylcholine.

The amount of lipid necessary to encapsulate and/or complex carmustine depends on the excipients and process conditions selected to form the complexes, but are in the range between 1:1 and 1:100 (compound:lipid), preferably between 1:1 and 1:25. The carmustine to lipid ratio, according to the highly preferred embodiment is in the range of 1:10 to 1:20. These drug lipid ratios are ideal to obtain the average particles size of the drug lipid complex less than 1,000 nm in diameter, preferably about 20-200 nm and more preferably less than 100 nm. Further according to the preferred embodiment of the present invention, this drug lipid ratio also helps in achieving an entrapment efficacy and/or complexation efficacy of 60% or more.

Further, according to the preferred embodiment of the present invention, other conventional adjuvants such as buffers, isotonic agents, pH adjusters, antioxidants, reducing agents, antimicrobial preservatives, freeze-dried excipients, stabilizers etc. are also employed in the preparation of said pharmaceutical preparation.

Buffering/PH adjusting agents according to present invention include, but are not limited to, hydrochloric acid, citric acid, tartaric acid, phosphoric acid, meta-phosphoric acid, poly-meta-phosphoric acid, carbonic acid, sodium hydroxide, potassium hydroxide, sodium citrate, potassium citrate, sodium bicarbonate potassium carbonate, amine, disodium hydrogen phosphate, dipotassium hydrogen phosphate, Disodium Succinate hexahydrate, monoethanolamine, diethanolamine, triethanolamine, 1,2-hexanediamine, sodium carbonate, sodium potassium tartrate, potassium metaphosphate, polyvinylidene potassium phosphate, sodium metaphosphate one or several. Preferably, pH of the pharmaceutical composition of the present invention is in the range of 8 or less, preferably a pH of 5.6±2. Disodium succinate hexahydrate is the preferred agent according to one aspect of the present invention. Further, the present inventors have also found that amount of buffer present in the formulation also plays important role in entrapment or complexation efficiency of the drug to lipid. Typically, the present formulation includes buffer in the range of up to 15% by weight and more preferably of about 10% by weight.

Supporting agents/osmogens which can be used in present invention are selected from, but not limited to mannitol, lactose, glucose, sorbitol, sodium chloride, hydrolyzed gelatin, dextran, sucrose, glycine, polyvinylpyrrolidone and the like. Typically, sucrose is the preferred osmotic agent, employed in the present formulation.

Preservatives may be selected from but not limited to alpha-tocopherol, phenol, cresol, tri-butanol, benzyl alcohol, and paraben. Typically, alpha tocopherol in the range of about 0.55 by weight is preferred as preservative.

Stabilizers/antioxidants to be used in present invention may be selected from, but not limited to, sodium sulfite, sodium bisulfite, sodium metabisulfite, sodium thiosulfate, thiourea, vitamin C, butylated hydroxy anisole, dibutyl phenol, propyl gallate, tocopherol, methionine, cysteine hydrochloride, acetyl cysteine, N-acetyl-DL-methionine, ascorbic palmitate, ethylenediaminetetraacetic acid, disodium edetate one or several.

The primary role of the surfactant is stabilization of the nanoparticles in the colloidal state and prevention of particle size growth during storage. The choice of stabilizers is an important parameter to be considered in optimizing any nanoparticle formulation, not only to control the particle size and stabilization of the dispersions but also to control the crystallization and polymorphic transitions. Surfactants which can be used in the formulation according to invention includes, but are not limited to, Polysorbates (Tween™), sodium cholesteryl sulfate (SCS), Sodium dodecyl sulfate, sodium lauryl sulfate, Lauryl dimethyl amine oxide, Cetyltrimethylammonium bromide (CTAB), Polyethoxylated alcohols, Polyoxyethylene sorbitan, Octoxynol (Triton X100™), N, N-dimethyldodecylamine-N-oxide, Hexadecyl trimethyl ammonium bromide (HTAB), Polyoxyl 10 lauryl ether, Brij 721™, Bile salts (sodium deoxycholate, sodium cholate), Polyoxyl castor oil (Cremophor™) Nonylphenol ethoxylate (Tergitol™), Cyclodextrins, Lecithin, Methylbenzethonium chloride (Hyamine™). Sodium cholesteryl sulfate is the preferred surfactant, according to one of the embodiment of the present invention and it is employed in the concentration ranges of up to 1% by weight.

The present invention also provides a process for manufacture of stable lipid suspension formulation of Carmustine for parenteral administration. Phase volume ratio (ratio of dispersed phase to continuous phase), surface characteristics (e.g. surface charge), entrapment efficacy, and particle size of the dispersed phase were found to be important factors in determining the stability of the composition of invention, pharmacokinetics of drug administered in suspension, and final efficacy of the product.

A typical process for manufacture of the said pharmaceutical preparation of Carmustine according to the present invention comprises of:
1. Preparation of buffer solution by dissolving buffering agent in suitable aqueous solvents;
2. Dispersing the lipid and other excipients in the buffer solution of step-1 to make lipid dispersion;
3. After dispersion, homogenization of lipid dispersion for reducing size;
4. Addition of carmustine in the lipid dispersion of step-2;
5. Homogenization/Extrusion of mixture obtained in step-3
6. Adjusting the volume and osmolality by addition of sucrose
7. Lyophilizing the solution of step—5 with suitable lyophilization process; and
8. Packing in suitable container closure system.

The lyophilized preparation of the present invention is filled in suitable container/closure system, e.g., ampoules, vials, prefilled syringe system, etc., which could be diluted with suitable diluent to prepare the suspension injection formulation ready to administer.

Typically, the pH of the buffer solution of the process according to present invention is about 5.6. The pH may be adjusted with use of hydrochloric acid or sodium hydroxide solution. Further suitable mixers and homogenizers are used to achieve uniform lipid dispersion. Typically, solution is homogenized at pressure range upto 20000 psi to achieve desired particle size. During this process temperature is controlled and kept at about 5° C. Lyophilization was carried out by using the process developed for the present invention.

For administration, lipid preparation according to the present invention may further comprise one or more pharmaceutically acceptable vehicle carriers therein. Such carriers may be selected from saline, sterile water, Ringer's solution, buffered saline, dextrose solution, maltodextrin solution, glycerol, ethanol and a combination thereof. The drug delivery system may be in the form of injections such as suspensions, emulsions, or injectable form of freeze-dried powder ready for reconstitution. Modifications in the above mentioned process can be made as known to the person skilled in the art.

Depending on purpose, the preparation according to the present invention may be administered by various parenteral ways, but not limited to intravenous, subcutaneous, intrathecal or intraperitoneal. The dose of the lipid suspension of present invention may vary depending on various factors including the weight, age, gender, and the state of health of the patients as well as on the diet, time of administration, route of administration, rate of excrement, and severity of illness. Preferably, anticancer agent loaded into lipids is administered at a dose of about 0.1-5 mg/kg weight (or 10-100 mg/m$^2$ body surface area) once a week for 3-4 weeks.

According to present invention, said pharmaceutical preparation is stable; wherein "stable pharmaceutical preparation" is defined as no aggregation observed when said pharmaceutical preparation is kept for stability studies at 2° C. to 8° C. (Real time study) and 25° C./60% relative humidity (Accelerated study) for at least 6 months and wherein the assay of Carmustine was at least 90%. Further the carmustine composition contains not more than about 0.1% of carmustine impurity A and the total known and unknown impurities in the present composition are less than about 1.0% by weight.

The assay of Carmustine in the said pharmaceutical preparation can be carried out by any of the methods known to the person skilled in the art, e.g. High performance liquid chromatography (HPLC), Spectrophotometry (UV spectrophotometry), Gas Chromatography (GC) etc.

Carmustine compositions of the present invention are useful for the treatment of brain tumors (glioblastoma, brainstem glioma, a medulloblastoma, astrocytoma, and room ependymoma), brain metastases and meningeal leukemia. It can also be used to treat malignant lymphoma, multiple myeloma, or in combination with other drugs for treatment of malignant melanoma.

EXAMPLES

A better understanding of present invention may be obtained through the following examples and process for manufacturing set forth to illustrate, but should not to be construed as limiting the present invention.

Example—1-7: Preparation of Carmustine Lipid Suspension for Injection

Composition:

|  | % w/w | | | | | | |
| --- | --- | --- | --- | --- | --- | --- | --- |
| Ingredients | Example-1 | Example-2 | Example-3 | Example-4 | Example-5 | Example-6 | Example-7 |
| Carmustine | 1.00 | 1.00 | 1.00 | 0.51 | 0.50 | 1.00 | 0.225 |
| Soybean phosphatidylcholine | 18.00 | 16.00 | 22.00 | 5.00 | 25.00 | 20.00 | 20.00 |
| Sodium Cholesteryl sulphate | 0.10 | 0.10 | 0.20 | 1.50 | 0.25 | 0.12 | 0.12 |
| Alpha Tocopherol | 0.02 | 0.02 | 0.02 | 0.00 | 0.00 | 0.02 | 0.02 |
| Sucrose | 5.00 | 10.00 | 20.00 | 8.00 | 8.00 | 8.00 | 8.0 |
| Disodium Succinate hexahydrate | 7.00 | 12.00 | 20.00 | 3.00 | 3.00 | 9.00 | 10.0 |
| Water for Injection | q.s. | q.s. | q.s. | q.s | q.s | q.s | q.s |

Above formulations were prepared by a typical process comprising following steps: Initially, Disodium succinate hexahydrate was dissolved in Water for Injection and pH was adjusted to 5.6 using 20% v/v HCl Solution. In 90% of buffer solution of Step 1, soybean phosphatidylcholine (SPC 90G) and Sodium Cholesteryl sulfate (Sodium Cholesteryl Sulfate) were mixed thoroughly, which was further homogenized for 20 minutes at 12600 to 14200 rpm till desired particle size achieved. Temperature of the solution was further cooled to the temperature of about 5° C. to 25° C. Accurately weighed amount of Carmustine was then added to Step 2 and mixed well. Homogenization/Extrusion of mixture obtained was further carried out. Weighed amount of Sucrose was then added to the remaining 10% buffer solution and was then added to the drug solution. Final volume was of the solution was adjusted. Measured volume of the solution was then filled in suitable vials and was lyophilized.

Example—8-9: Preparation of Lipid Suspension

|  | % w/w | |
| --- | --- | --- |
| Ingredients | Example-8 | Example-9 |
| Carmustine | 0.51 | 0.50 |
| Dimyristoylphosphatidylcholine | 8.00 | 10 |
| Sodium Cholesteryl Sulfate | 0.12 | — |
| Alpha Tocopherol | 0.02 | 0.03 |
| Sucrose | 8.00 | 8.00 |
| Disodium Succinate hexahydrate | 3.00 | 3.00 |
| HCl | q.s | q.s. |
| Water for Injection | q.s. | q.s. |

The above compositions are suitably formulated by using process as described for example 1 to 7.

Example—10: Evaluation of Lipid Formulation

The above formulation of Example 6 was evaluated for various parameters and results are summarized in below table.

The above formulation was evaluated for various parameters and results are summarized in below table.

|  | Initial | 2°-8° C./1M | 2°-8° C./2M | Initial | 2°-8° C./1M | 2°-8° C./2M |
| --- | --- | --- | --- | --- | --- | --- |
| Description | Light Yellow lipid suspension | Complies | Complies | Complies | Complies | Complies |
| pH | 5.7 | 5.7 | 5.7 | 5.6 | 5.6 | 5.6 |
| Z- Avg. Particle size (nm) | 57.3 | — | 55.9 | 48.8 | — | 50.4 |
| % Drug Entrapment | 75.9 | 74.6 | 75.9 | 77.1 | 77.3 | 78.1 |

We claim:

1. A stable lipid suspension composition comprising a lyophilized powder comprising carmustine, a buffer and a lipid wherein the ratio of carmustine to lipid is from about 1:1 to about 1:25 and the lipid encapsulates or complexes the carmustine and the lipid encapsulated or complexed carmustine has a particle size of less than 200 nm.

2. The stable lipid suspension composition as claimed in claim 1, wherein the composition further comprises one or more pharmaceutical acceptable excipients selected from the group consisting of isotonic agents, pH adjusters, antioxidants, reducing agents, surfactants, antimicrobial preservatives, freeze-dried excipients, or stabilizers.

3. The stable lipid suspension composition as claimed in claim 1, wherein the ratio of carmustine to lipid is from about 1:10 to about 1:25.

4. The stable lipid suspension composition as claimed in claim 1, wherein the ratio of carmustine to lipid is about 1:20.

5. The stable lipid suspension composition as claimed in claim 1, wherein the lipid is selected from the group consisting of lecithin, sphingosylphosphorylcholine, soybean phosphatidylcholine, dipalmitate phosphatidylcholine, hydrogenated soy lecithin, phosphatidic acid or phosphatidylserine ethanolamine, egg phosphatidylcholine, egg phosphatidyl-glycerol, dimyristoyl-phosphatidyl-glycerol, dimyristoyl-phosphatidylcholine, hydrogenated soy phosphatidylcholine.

6. The stable lipid suspension composition as claimed in claim 1, wherein the particle size of carmustine lipid complex is less than 100 nm.

7. The stable lipid suspension composition as claimed in claim 1, wherein the buffer is selected from the group consisting of hydrochloric acid, citric acid, tartaric acid, phosphoric acid, meta-phosphoric acid, poly-meta-phosphoric acid, carbonic acid, sodium hydroxide, potassium hydroxide, sodium citrate, potassium citrate, sodium bicarbonate potassium carbonate, amine, disodium hydrogen phosphate, dipotassium hydrogen phosphate, disodium succinate hexahydrate, monoethanolamine, diethanolamine, triethanolamine, 1,2-hexanediamine, sodium carbonate, sodium potassium tartrate, potassium metaphosphate, polyvinylidene potassium phosphate, sodium metaphosphate and combinations thereof.

8. The stable lipid suspension composition as claimed in claim 7, wherein the buffer is disodium succinate hexahydrate and is present up to 15% by weight of the composition.

9. A process for preparation of the stable lipid suspension composition as claimed in claim 1, comprising the steps of:
   a) preparing a buffer solution by dissolving a buffering agent in suitable aqueous solvents;
   b) dispersing the lipid and other excipients in the buffer solution of step a to make a lipid dispersion;
   c) homogenizing the lipid dispersion for reducing size;
   d) adding carmustine to the lipid dispersion;
   e) homogenizing/extruding the mixture obtained in step d;
   f) adjusting the volume and osmolality of the mixture of step d or e by addition of sucrose and suitable vehicle;
   g) lyophilizing the mixture of step f; and
   h) packing the lyophilized mixture in suitable container closure system.

10. A lyophilized carmustine composition suitable for dilution with aqueous vehicles comprising:
   (i) carmustine:
   (ii) a buffer selected from the group consisting of hydrochloric acid, citric acid, tartaric acid, phosphoric acid, meta-phosphoric acid, poly-meta-phosphoric acid, carbonic acid, sodium hydroxide, potassium hydroxide, sodium citrate, potassium citrate, sodium bicarbonate potassium carbonate, amine, disodium hydrogen phosphate, dipotassium hydrogen phosphate, disodium succinate hexahydrate, monoethanolamine, diethanolamine, triethanolamine, 1,2-hexanediamine, sodium carbonate, sodium potassium tartrate, potassium metaphosphate, polyvinylidene potassium phosphate, sodium metaphosphate and combinations thereof
   (iii) a lipid selected from the group consisting of lecithin, sphingosylphosphorylcholine, soybean phosphatidylcholine, dipalmitate phosphatidylcholine, hydrogenated soy lecithin, phosphatidic acid or phosphatidylserine ethanolamine, egg phosphatidylcholine, egg phosphatidyl-glycerol, dimyristoyl-phosphatidyl-glycerol, dimyristoyl-phosphatidylcholine, hydrogenated soy phosphatidylcholine;
   (iv) a preservative or antioxidant selected from the group consisting of alpha-tocopherol, phenol, cresol, tri-butanol, benzyl alcohol, and paraben, sodium sulfite, sodium bisulfite, sodium metabisulfite, sodium thiosulfate, thiourea, vitamin C, butylated hydroxy anisole, dibutyl phenol, propyl gallate, tocopherol, methionine, cysteine hydrochloride, acetyl cysteine, N-acetyl-DL-methionine, ascorbic palmitate, ethylenediaminetetraacetic acid, disodium edetate;
   (v) a surfactant selected from the group consisting of polysorbates, sodium cholesteryl sulfate, sodium dodecyl sulfate, lauryl dimethyl amine oxide, cetyltrimethylammonium bromide, polyethoxylated alcohols, polyoxyethylene sorbitan, octoxynol, N, N-dimethyldodecylamine-N-oxide, hexadecyl trimethyl ammonium bromide, polyoxyl 10 lauryl ether, bile salts, polyoxyl castor oil, nonylphenol ethoxylate, cyclodextrins, methylbenzethonium chloride and combinations thereof; and
   (vi) an osmogen selected from the group consisting of mannitol, lactose, glucose, sorbitol, sodium chloride, hydrolyzed gelatin, dextran, sucrose, glycine, polyvinylpyrrolidone;
   wherein the ratio of carmustine to lipid is from about 1:10 to about 1:25 and the lipid encapsulates or complexes the carmustine and the lipid encapsulated or complexed carmustine has a particle size of less than 100 nm.

11. The lyophilized carmustine composition of claim 10 wherein the buffer comprises disodium succinate hexahydrate.

12. The lyophilized carmustine composition of claim 10 wherein the lipid comprises soybean phosphatidylcholine, dimyristoyl-phosphatidylcholine or a combination thereof.

13. The lyophilized carmustine composition of claim 10 wherein the preservative or antioxidant comprises alpha-tocopherol.

14. The lyophilized carmustine composition of claim 10 wherein the surfactant comprises sodium cholesteryl sulfate.

15. The lyophilized carmustine composition of claim 10 wherein the osmogen comprises sucrose.

16. A process for preparing the lyophilized composition as claimed in claim 10, comprising the steps of:
   a) preparing a buffer solution by dissolving the buffer in suitable aqueous solvents;
   b) dispersing the lipid in the buffer solution of step a to make a lipid dispersion;
   c) homogenizing the lipid dispersion for reducing size;
   d) adding carmustine to the lipid dispersion;
   e) homogenizing/extruding the mixture obtained in step d;
   f) adjusting the volume and osmolality of the mixture of step d or step e by addition of the osmogen in a suitable vehicle;
   g) lyophilizing the mixture of step f; and
   h) packing the lyophilized mixture in suitable container closure system.

17. The lyophilized carmustine composition of claim 10 wherein the buffer comprises disodium succinate hexahydrate; the lipid comprises soybean phosphatidylcholine, dimyristoyl-phosphatidylcholine or a combination thereof;

the preservative or antioxidant comprises alpha-tocopherol; the surfactant comprises sodium cholesteryl sulfate; and the osmogen comprises sucrose.

18. A process for preparing the lyophilized composition as claimed in claim 17, comprising the steps of:
   a) preparing a buffer solution by dissolving the disodium succinate hexahydrate in suitable aqueous solvents;
   b) dispersing the disodium succinate hexahydrate in the buffer solution of step a to make a lipid dispersion;
   c) homogenizing the lipid dispersion for reducing size;
   d) adding carmustine to the lipid dispersion;
   e) homogenizing/extruding the mixture obtained in step d;
   f) adjusting the volume and osmolality of the mixture step d or step e by addition of the sucrose in a suitable vehicle;
   g) lyophilizing the mixture of step f; and
   h) packing the lyophilized mixture in suitable container closure system.

* * * * *